US010578558B2

(12) United States Patent
Garrote Contreras et al.

(10) Patent No.: US 10,578,558 B2
(45) Date of Patent: Mar. 3, 2020

(54) METHODS AND SYSTEMS FOR VISUAL INSPECTION

(71) Applicants: FUNDACION TECNALIA RESEARCH & INNOVATION, Donostia-San Sebastián (ES); UNIVERSIDAD DEL PAÍS VASCO-EUSKAL HERRIKO UNIBERTSITATEA, Leioa (ES)

(72) Inventors: Estibaliz Garrote Contreras, Derio (ES); Alberto Isasi Andrieu, Derio (ES); Gorka Duro Rodriguez, Derio (ES); Pedro María Iriondo Bengoa, Leioa (ES)

(73) Assignees: FUNDACION TECNALIA RESEARCH & INNOVATION, Donostia-San Sebastian (ES); UNIVERSIDAD DEL PAIS VASCO-EUSKAL HERRIKO UNIBERTSITATEA, Leioa (ES)

( * ) Notice: Subject to any disclaimer, the term of this patent is extended or adjusted under 35 U.S.C. 154(b) by 0 days.

(21) Appl. No.: 16/227,749

(22) Filed: Dec. 20, 2018

(65) Prior Publication Data

US 2019/0187066 A1 Jun. 20, 2019

(30) Foreign Application Priority Data

Dec. 20, 2017 (EP) .................................. 17382869

(51) Int. Cl.
*G01N 21/88* (2006.01)
*G01N 21/95* (2006.01)
*G01B 11/26* (2006.01)

(52) U.S. Cl.
CPC ......... *G01N 21/8806* (2013.01); *G01B 11/26* (2013.01); *G01N 21/8803* (2013.01);
(Continued)

(58) Field of Classification Search
CPC .......... G01N 21/8806; G01N 21/8803; G01N 21/9515; G01N 2021/8835; G01N 2201/06113; G01B 11/26
(Continued)

(56) References Cited

U.S. PATENT DOCUMENTS 4,548,506 A * 10/1985 Elson ................... G01B 11/303
356/446
4,575,244 A * 3/1986 Kaffka ................. G01N 21/474
356/343

(Continued)

FOREIGN PATENT DOCUMENTS

CN 201313071 Y 9/2009
CN 104034261 A 9/2014
(Continued)

OTHER PUBLICATIONS

Lee et al., Multi-Beam laser probe for measuring position and orientation of freeform surface, Measurement 44 (2011) 1-10, 10 pages.
(Continued)

*Primary Examiner* — Isiaka O Akanbi
(74) *Attorney, Agent, or Firm* — Edell, Shapiro & Finnan, LLC

(57) ABSTRACT

Systems for visually inspecting a surface of an object are provided, which includes a visual inspection head, and a positioning apparatus for controlling a position and/or an orientation of the visual inspection head with respect to the object. The visual inspection head includes a visual inspection module, and an angle controlling module for ensuring a predetermined angle of the visual inspection system with respect to an area to be inspected of the surface of the object. The angle controlling module may include a pointer for projecting a light beam onto the area to be inspected and a camera for determining whether the light beam is reflected
(Continued)

substantially perpendicularly. The system is configured to move the visual inspection head relative to the object until the light beam is reflected substantially perpendicularly. Methods for visually inspecting a surface are also provided.

20 Claims, 3 Drawing Sheets

(52) U.S. Cl.
CPC . *G01N 21/9515* (2013.01); *G01N 2021/8835* (2013.01); *G01N 2201/06113* (2013.01)

(58) Field of Classification Search
USPC .................. 356/237.2–237.6, 600, 445–448
See application file for complete search history.

(56) References Cited

U.S. PATENT DOCUMENTS

| | | | | |
|---|---|---|---|---|
| 4,673,818 A | * | 6/1987 | Guerra | G01B 11/303 |
| | | | | 250/228 |
| 4,954,722 A | * | 9/1990 | Fine | G01B 11/303 |
| | | | | 250/216 |
| 5,912,741 A | * | 6/1999 | Carter | G01N 21/4738 |
| | | | | 356/445 |
| 6,304,050 B1 | | 10/2001 | Skaar et al. | |
| 7,649,628 B2 | * | 1/2010 | Wadman | G01N 21/4738 |
| | | | | 356/445 |
| 7,872,754 B2 | * | 1/2011 | Wadman | A61B 5/0059 |
| | | | | 356/445 |
| 2007/0122026 A1 | | 5/2007 | Ersue et al. | |
| 2013/0063590 A1 | | 3/2013 | Deppe et al. | |

FOREIGN PATENT DOCUMENTS

| | | |
|---|---|---|
| DE | 102008002519 A1 | 12/2009 |
| JP | S6337204 A | 2/1988 |
| JP | 2001099632 A | 4/2001 |
| JP | 2006300763 A | 11/2006 |
| JP | 2008046103 A | 2/2008 |
| KR | 20020070192 A | 9/2002 |
| WO | 9208103 A1 | 5/1992 |
| WO | 2009065227 A1 | 5/2009 |

OTHER PUBLICATIONS

Extended European Search Report in corresponding European Application No. 17382869.0, dated Jun. 12, 2018.

* cited by examiner

METHODS AND SYSTEMS FOR VISUAL INSPECTION

CROSS-REFERENCE TO RELATED APPLICATIONS

This application relates to and claims the benefit and priority to European Application No. EP17382869, filed Dec. 20, 2017.

TECHNICAL FIELD

The present disclosure relates to methods and systems for visual inspection of objects. More particularly, the present disclosure relates to methods and systems for visual inspection that allow visual inspection systems to be positioned and/or oriented in a predetermined manner with respect to an area of a surface of the object to be inspected.

BACKGROUND

Quality control of products can be an important aspect of manufacturing processes. A part of quality control in an industrial or manufacturing setting can include a visual inspection of a product that has been manufactured. In particular, visual inspection can relate to a visual inspection of a surface of a product. The objective of such a visual inspection is inter alia to check for possible defects or irregularities on a surface. If such defects are identified, and depending on the gravity of the defects, the product is normally to be discarded or repaired. The defects in this sense may be purely aesthetic but they can also be functional in that they would affect the use or operation of a product.

Different techniques are known for such a visual inspection of a surface to detect irregularities or defects. The techniques may be based on projecting a light onto a surface to be inspected and measuring a reflection of the light projected onto the surface. Depending on the type of surface, the reflection can be (or can expected to be) diffuse or specular. The angle between the normal of the surface and the light, and the angle between such normal and the camera are the usual parameters to be controlled.

A particular case is deflectometry. It is one such visual inspection technique that is used particularly for specular surfaces.

In general, deflectometry refers to procedures used to acquire topographical information on specular surfaces by the analysis of a reflected image of a known pattern projected onto the surface. A (potential) irregularity or defect is detected by comparing an expected reflection pattern with an actual reflection pattern. When the deviation of the actual reflection is above a predetermined threshold, a (potential) defect may be identified.

Deflectometry has been applied e.g. in the aviation and automotive industry. In these cases, rather large specular surfaces of relatively minor curvature are to be inspected. In order for deflectometry to give reliable results, it is important that the position and/or orientation of the source projecting the pattern onto the surface with respect to the area of the surface to be inspected is well controlled. If the projection with respect to the normal to the surface at the inspection point is not accurately controlled, the expected reflection cannot be well defined either. This can lead to both "false positives" (a potential defect is identified whereas in reality there is no such defect) and "false negatives" (a potential defect is not identified whereas in reality there is a defect).

The requirement of the precise determination of the position and orientation of the origin of the projection with respect to the normal to the surface becomes much more important when smaller objects with surfaces with significant curvature and/or doubly curved surfaces are to be inspected. It has been found that when known deflectometry techniques are used on more complexly curved surfaces, the results are unsatisfactory.

The need for a precise determination of position and/or orientation of the projection with respect to a normal to the surface at the inspection point is not specific for deflectometry, but is also important for other visual inspection techniques, particularly when the objects to be inspected become smaller and when they have more complexly curved surfaces.

The present disclosure provides examples of methods and systems for visual inspection that can improve visual inspection techniques.

SUMMARY

In a first aspect, a system for visually inspecting a surface of an object is provided. The system comprises a visual inspection head, and a module for controlling a position and/or an orientation of the visual inspection head with respect to the object.

The visual inspection head comprises a visual inspection module, and an angle controlling module for ensuring a predetermined angle of the visual inspection head with respect to an area to be inspected of the surface of the object. The visual inspection module comprises a light source for projecting onto the surface and a sensor for determining a reflection from the surface. The angle controlling module comprises a pointer for projecting a light beam onto the area to be inspected, and a camera for determining whether the light beam is reflected substantially perpendicularly. The system is configured to move the visual inspection head relative to the object until the light beam is reflected substantially perpendicularly.

With a system according to this aspect, reliable visual surface inspection of increasingly complex objects becomes possible. The reliability of visual inspection techniques based on projecting a light or pattern onto a surface and measuring the reflection is highly dependent on knowing the correct position of the various elements including (the normal to the) surface to be inspected, the light source, and a receiving sensor. If the light source is oriented at an angle different from the supposed angle relative to the surface, the measured reflection will be interpreted wrongly. With objects of smaller size and complex curvature, the need to correctly orient the light source becomes increasingly important.

By using a pointer and determining whether the reflection is substantially perpendicular, the arrangement of the visual inspection head (which also includes the light source for projecting a pattern onto the surface) with respect to the surface normal can be ensured. Checking whether the reflection is perpendicular (rather than at other angles) has the additional effect that the reflection is independent from the height or distance of the visual inspection head with respect to the object.

With the system according to this aspect, any device for visually inspecting a surface of an object can be positioned (and can remain positioned) perpendicular to the surface at each inspection point independently of the distance to such a surface or inspection point. Correct positioning during scanning can be ensured all times.

In a second aspect, a system for visually inspecting a surface of an object is provided. The system comprises a visual inspection head, and a module for controlling an orientation of the visual inspection head with respect to the normal to the surface in the inspection point. The visual inspection head comprises a visual inspection module and an angle measurement module for determining an angle of the visual inspection head with respect to an area to be inspected of the surface of the object. The visual inspection module comprises a light source for projecting onto the surface and a sensor for determining a reflection from the surface, and the angle measurement module comprises a pointer for projecting a light beam onto the area to be inspected, a receiving surface for receiving the light beam after reflecting from the area to be inspected, and a camera for determining a position of the reflected light beam on the receiving surface.

By using a pointer and determining a position of a reflection from the pointer on a receiving surface, a wide variety of reflection angles can be measured. The relative position to the surface normal can thus be known. By integrating the visual inspection module, and the angle measurement module for determining an angle of the visual inspection system with respect to an area to be inspected in the same head, and also providing a module for controlling an orientation of the visual inspection head, the correct positioning of the system can be ensured.

Throughout the present disclosure, the terms "normal to a surface" and "surface normal" are used interchangeably, and both refer to a vector that is perpendicular to the tangent plane to a surface in a specific point.

In some examples, the pointer may be a laser pointer.

In some examples, the pointer may be positioned on a first side of the receiving surface and the object is positioned on an opposite side of the receiving surface, the receiving surface comprising a hole for projection from the pointer onto the object. In these examples, perpendicularity of the (laser) pointer with respect to the surface area can be measured independently from a height (distance) of the visual inspection head with respect to the object. Perpendicularity is given when the laser reflected from the surface is received on the receiving surface in a small area surrounding the hole or inside the hole. There is thus no need to measure or know the distance of the visual inspection head with respect to the object to be inspected.

In some examples, the angle measurement module may further include an optic element to deviate the reflected light beam towards the receiving surface. Such optic elements may include mirrors and/or lenses. The optical elements optionally may be chosen in such a way that the laser beam passes through them towards the object without being deflected, whereas the reflected laser beam is deflected towards the receiving surface.

In some examples, the module for controlling an orientation of the visual inspection head with respect to the object may have actuators for moving the object. In other examples, the system for changing an orientation of the visual inspection head with respect to the object comprises actuators for moving the visual inspection head. In yet further examples, both may be combined. In an industrial setting for rapidly inspecting products that are produced in series, it may be more suitable to have a module for controlling an orientation and/or position of the visual inspection head with respect to the object. Such a module may be or may form part of a robotic arm. In other examples, it might be more suitable to place an object to be inspected in a clamp with sufficient degrees of freedom to reposition and/or reorient the object itself.

In some examples, the visual inspection head may comprise a positioning module for changing an angle of the light source for projecting onto the surface and of the sensor for determining a reflection from the surface. Depending on the technique used, and depending on the surface to be inspected, it might be desirable to change the orientation of the light source and receiver with respect to the surface to be inspected. For example, in deflectometry, the angle at which a pattern is projected onto the surface may be changed in accordance with a specific implementation. Once an angle has been set for a specific surface or area of a surface, the angle measurement module commented before can ensure that the correct angle is maintained.

In a further aspect, a method for visually inspecting a surface of an object is provided. The method comprises consecutively scanning different areas of the surface of the object by projecting a light onto the areas and sensing a reflection from the areas. The scanning comprises (before projecting the light and sense the reflection) on each of the consecutive areas, determining an instantaneous angle of the light with respect to the surface of the area and comparing the instantaneous angle with a predetermined angle. The angle of the light with respect to the surface of the area is adjusted if a difference between the instantaneous angle and the predetermined angle is above a threshold.

Herein the determination of the instantaneous angle includes projecting a laser beam on the area, receiving the laser beam reflection, and determining whether the laser beam has been reflected substantially perpendicularly.

If the laser beam has been reflected substantially perpendicularly, then the laser beam (and thus also the light used for projection in the surface scanning) is positioned correctly.

In yet a further aspect, a method for visually inspecting a surface of an object is provided. The method comprises consecutively scanning different areas of the surface of the object by projecting a light onto the areas and sensing a reflection from the areas. The scanning comprises prior to projecting the light for each of the areas determining an instantaneous angle of the light with respect to the surface of the area and comparing the instantaneous angle with a predetermined angle. The method further comprises adjusting the angle of the light with respect to the surface of the area if a difference between the instantaneous angle and the predetermined angle is above a threshold. Determining the instantaneous angle comprises projecting a laser beam on the area, receiving the laser beam reflection on a receiving surface, measuring a position of the laser beam reflection on the receiving surface and determining the instantaneous angle of the laser beam with respect to the surface based on the position of the laser beam reflection.

With methods according to these aspects, surface inspection of in particular specular surfaces may be improved. Inspection of surfaces which are not curved, have a relatively small curvature or are not very complex can be improved with such a method, whereas inspection of complex surfaces with complex curvature is actually made possible.

In some examples, the method may further comprise comparing the instantaneous angle of the (reflected) laser beam with a predetermined angle for the (reflected) laser beam.

In some examples comparing the instantaneous angle of the (reflected) laser beam with a predetermined angle for the (reflected) laser beam comprises comparing the position of the laser beam reflection with a predetermined area of a receiving surface. If a height of the laser beam with respect to the object, and a height of the receiving surface with respect to the object are constant, each area of the receiving surface upon which the reflected laser beam is received corresponds to a specific angle of the laser beam with respect to the (normal of) the surface. Instead of particularly calculating the instantaneous angle, depending on the implementation, it may be sufficient to check whether the reflected laser beam falls within a predetermined area, and if not, move the visual inspection head relatively to the object until this condition is satisfied.

In some examples, the method may further comprise determining a height of the laser beam with respect to the area. Measuring the height (or distance) of the laser beam with respect to the object makes it possible to determine an absolute value of the laser beam with respect to the surface normal from the position of the reflected laser beam. If the angle for the laser beam used for angular measurement is to be maintained at 90°, the height of the laser beam with respect to the object does not need to be taken into account. For other settings, the height of the laser beam with respect to a local surface area may be measured and taken into account to correctly determine the angle and if necessary adjust the angle of the light with respect to the surface of the area.

BRIEF DESCRIPTION OF THE DRAWINGS

Non-limiting examples of the present disclosure will be described in the following, with reference to the appended drawings, in which.

DETAILED DESCRIPTION

Figure 1A:
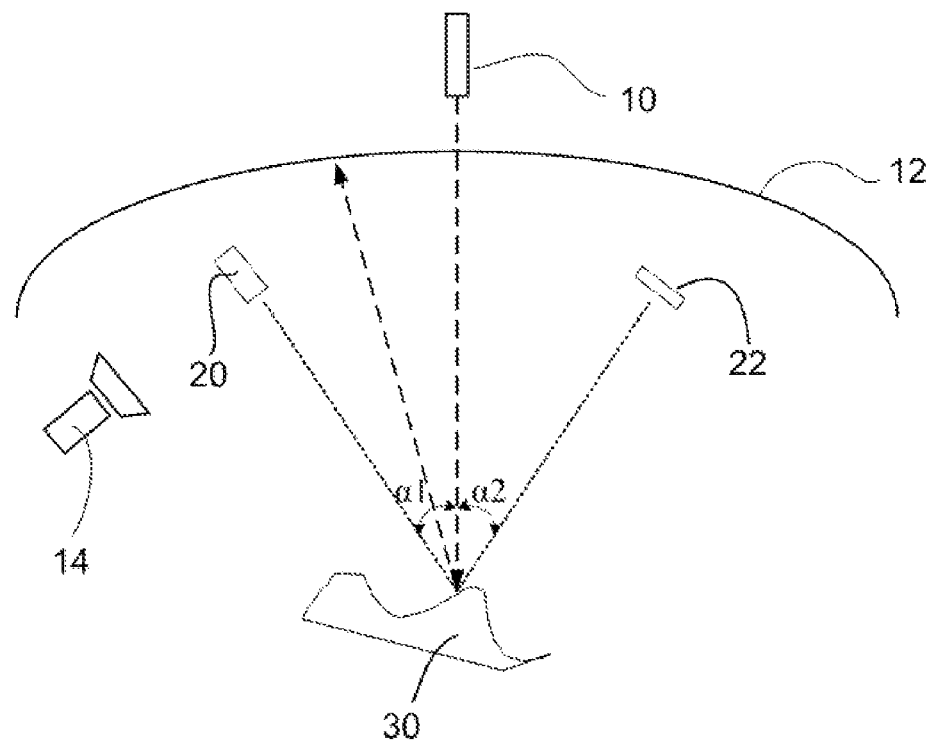
FIGS. 1A and 1B schematically illustrate an example of a visual inspection head in two different orientations with respect to an object to be inspected.
Figure 1B:
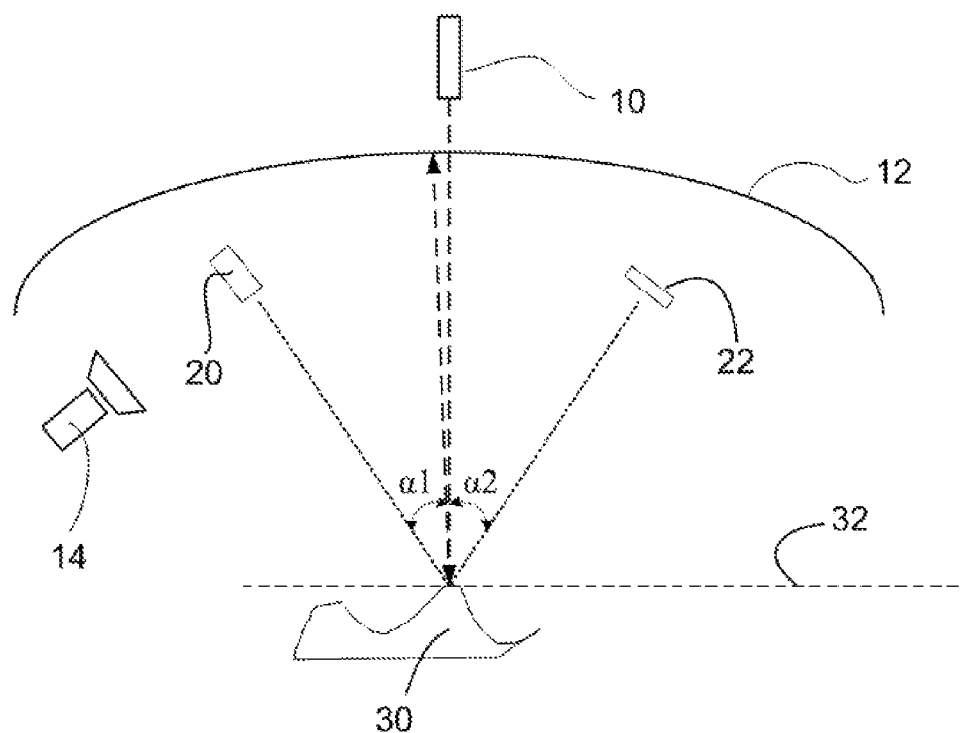

FIGS. 1A and 1B schematically illustrate an example of a visual inspection head in two different orientations with respect to an object to be inspected. A system according to the present disclosure may include a visual inspection head such as disclosed in FIGS. 1A and 1B, and a system for reorienting and/or repositioning the visual inspection head with respect to the object. For example, the visual inspection head may be integrated in a robotic arm with sufficient degrees of freedom to scan the surface of the object to be inspected.

The visual inspection head in this example comprises laser pointer 10, and a curved receiving surface 12. The curvature of the receiving surface depicted in FIG. 1a is only schematic. The receiving surface might be more curved than shown, and it may have a constant curvature to form a dome with e.g. a semi-circular cross-section. In other examples, the receiving surface might be flat.

The laser pointer 10 projects a laser spot onto a local surface area of object 30. Depending on the angle of incidence of the laser beam, the reflection will vary. The reflected laser beam is received at receiving surface 12 and camera 14 may determine the precise location of the reflection. In this example, camera 14, receiving surface 12 and laser pointer 10 together form the angle measurement module of the depicted visual inspection head. Depending on the location of the reflected laser beam, the angle of the laser pointer 10 with respect to a local surface (normal) may be determined. If the angle is not the desired angle, the visual inspection head may be moved or rotated relative to the object.

In order to determine the absolute value of the angle of the laser pointer 10 with respect to the local surface normal, the distance of the laser pointer with respect to the surface would have to be known. In some examples, it is not necessary to know the absolute value of the angle of the laser pointer. Rather, the location of the reflected laser beam may simply be compared to a predetermined area on the receiving surface 12. If the reflection falls within predetermined boundaries, the angle of the laser beam is deemed to be acceptable. If the reflection falls outside such boundaries, the angle of the laser beam is not acceptable or correct.

In the example of FIG. 1A, the laser pointer is arranged on a back side of the receiving surface, i.e. the object to be inspected is at the opposite side of the receiving surface. The receiving surface to this end may comprise a through-hole to let the laser beam pass.

Also provided in the visual inspection head of this example is a visual inspection module which comprises a light source 20 and a sensor 22 for receiving the reflection of the light projected onto object 30. The light source 20 in this example is arranged at an angle $\alpha 1$ with respect to the laser beam, and the sensor 22 is ranged at an angle $\alpha 2$ with respect to the laser beam. These angles $\alpha 1$ and $\alpha 2$ may be different or may be the same.

The light source 20 may further include e.g. grids or other elements to project a desired pattern onto object 30. Sensor 22 may include a camera for determining the reflection of the pattern. A deviation from an expected reflected pattern may indicate a surface irregularity. It is therefore important to establish the suitable angles $\alpha 1$ and $\alpha 2$ with respect to the local (normal of) the area to be inspected.

In the situation shown in FIG. 1A, it may be found that the laser pointer is not at a desired angle with respect to a local surface area of the object. This implies that the visual inspection head is not at a desired angle with respect to the (normal of the) local surface area. Thus, the light source 20 and sensor 22 used in visual inspection are not at a desired angle.

In one example, the visual inspection head may be repositioned relative to the object (or the object is repositioned with respect to the visual inspection head) until the desired angle of the laser beam with respect to the local surface area is achieved. For example, in FIG. 1b, the laser pointer and the object have such relative positions and orientations that a 90° angle is formed. This is one possible example of a desired angle. When the desired angle is achieved, the visual inspection system is also correctly oriented with respect to the local area of the surface to be inspected.

The visual inspection head may be integrated in e.g. a robotic arm. By controlling the robotic arm, the position and orientation of the visual inspection head with respect to object 30 may suitable be varied. In other examples, the object 30 may be held by e.g. a gripper. By moving and rotating the gripper, the position of the object may be varied with respect to the visual inspection head.

In FIG. 1b, tangent 32 to the local surface area has been indicated. When choosing a 90° angle for the laser pointer with respect to the local area (i.e. the laser beam substantially corresponds to the surface normal), the reflected laser beam on the receiving surface should be in a very small area surrounding the through-hole through which the laser beam passes. Moreover, when choosing a 90° angle, there is no need to determine a height of the laser pointer with respect to the object (i.e. the distance between the laser pointer and the object), as regardless of the height, the reflected laser beam should be in the same spot, or within the same small area.

By choosing the angle at 90°, the effect that the distance between the visual inspection head and the object has on the reflection is removed. A perpendicular reflection will always be in the same position on the receiving surface regardless of the distance.

In order to ensure a suitable distance, when a light pattern is projected by source 20, sensor 22 should receive a reflection. If none, or hardly any reflection is measured, this can mean that the height of the visual inspection module is inappropriate. The visual inspection head may thus be moved closer to the object or further away from the object to position it at a suitable height. Other methods for measuring a height may also be used. Such methods may include measuring a delay between sending a beam and receiving a reflection.

In another example, from the reflected laser beam, the angle of the laser pointer with respect to the local surface area (normal) can be calculated and then the visual inspection system 20, 22 may be repositioned to achieve a desired angle. The light source 20 and sensor 22 may be repositioned individually or in a system that controls the position of both at the same time. In both alternatives, reliable surface inspection can be achieved.

Figure 2A:
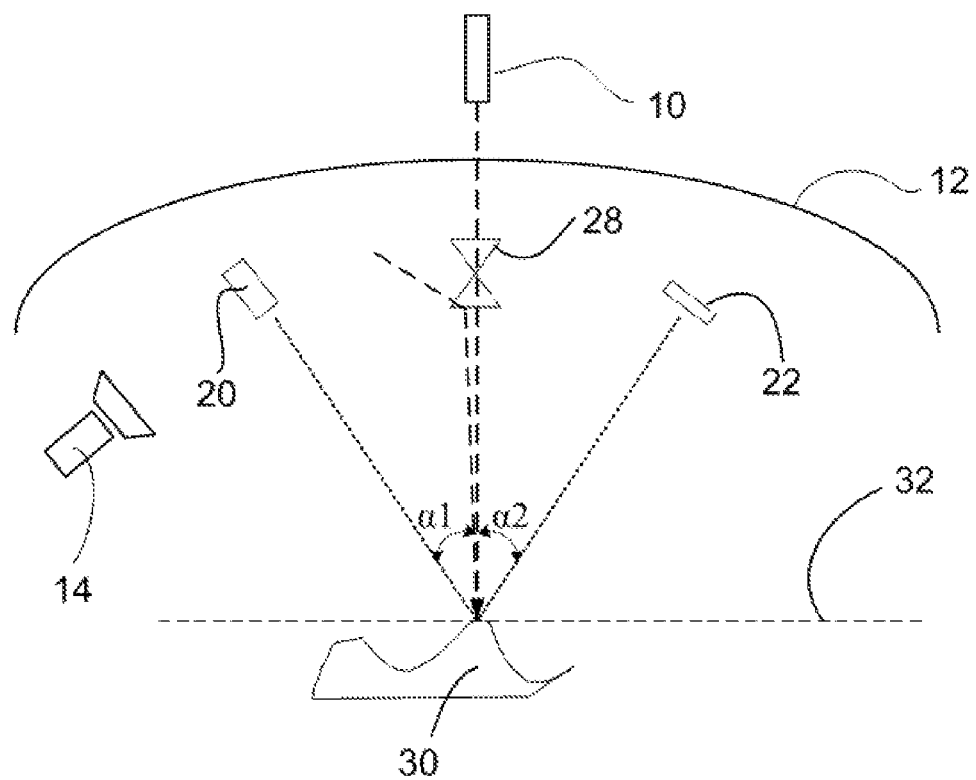
FIGS. 2A and 2B schematically illustrate further examples of a visual inspection head.

FIG. 2a schematically illustrates a further example of a visual inspection head. The visual inspection head is generally similar to the example of FIGS. 1a and 1b. The main difference in the example of FIG. 2a is that one or more optical elements 28 may be arranged between the object and the receiving surface. Such optical elements 28 may include mirrors and lenses. The optical elements 28 may also be arranged along a path in between the laser pointer and the object. The optical elements 28 may further be such that the laser beam from the laser pointer passes through without refraction or deflection, but the reflected laser beam is deflected on its path from the object towards the receiving surface. The deviation characteristics of the optical elements 28 should be known to determine the angle (and/or position) of the laser pointer with respect to the local (normal of) surface area.

Although in the depicted examples, the laser pointer is arranged on a side of the receiving surface that is opposite to the side where the object is located, this does not need to be the case. In particular, the use of optical elements 28 can ensure that the deflected laser beam does not interfere with the laser pointer itself.

Figure 2B:
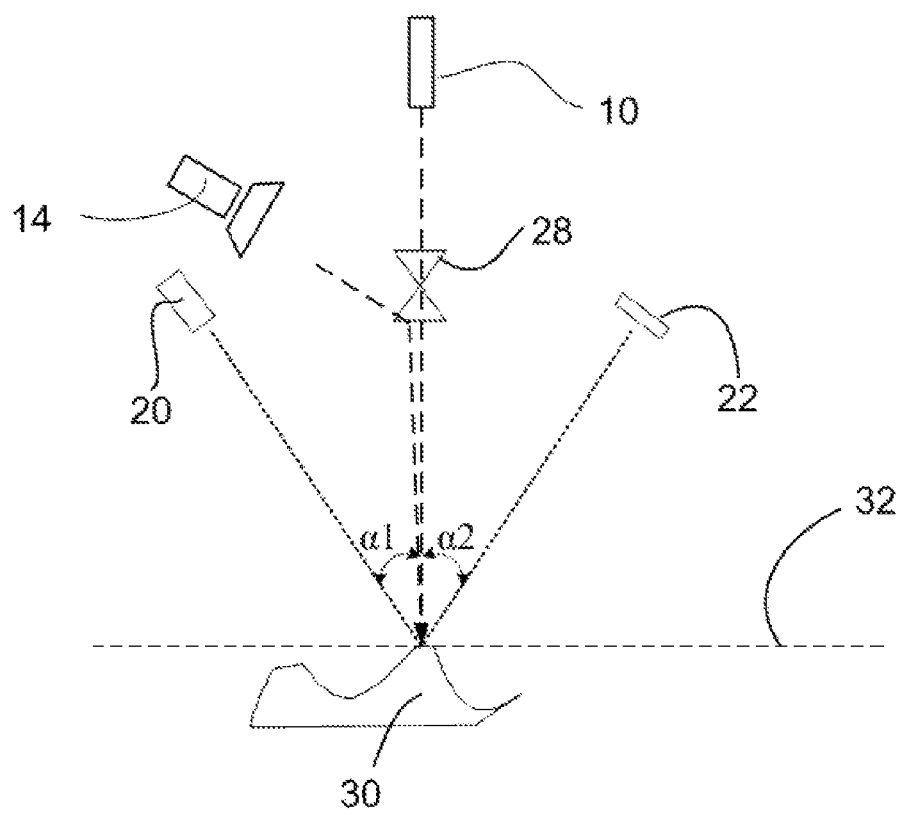

FIG. 2b schematically illustrates yet a further example of a visual inspection head. Contrary to the other examples, the visual inspection head does not include a receiving surface for receiving the reflected laser beam. In the example of FIG. 2b, the reflected laser beam is deviated towards camera 14 directly.

Figure 3:
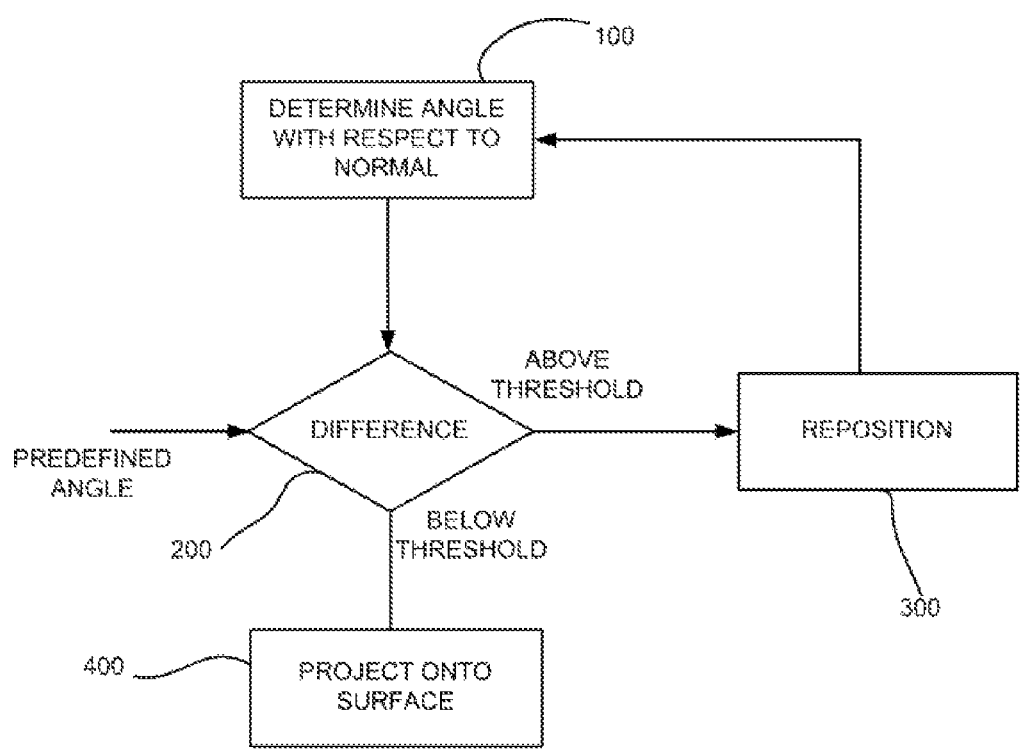
FIG. 3 schematically illustrates an example of a method for visually inspecting a surface of an object.

One method for visually inspecting a portion of a surface is schematically indicated in FIG. 3. It is based on the principle of the visual inspection module and angle measurement module being integrated in the same visual inspection head, and not reorienting one or the other with respect to the visual inspection head.

At block 100, prior to projecting a light (pattern) onto an area of the surface to be inspected, the angle of the laser pointer with respect to the area (and thereby the angle of the visual inspection module with respect to the surface normal) is determined. Determining the angle may include determining a distance between the laser pointer and the point of the object that is to be inspected, so that a precise value of the laser pointer with respect to the surface normal can be determined.

At block 200, the instantaneous angle is compared to a predefined angle. If the difference between the instantaneous angle and the predefined angle is higher than a threshold, prior to visually inspecting, the head needs to be repositioned or reoriented relatively to the object at block 300. Again, the instantaneous angle may be determined. This process may continue until the difference between the predefined angle and the instantaneous angle is below a threshold.

The instantaneous angle can be the angle of the laser pointer with respect to the surface normal or the instantaneous angle of the visual inspection head with respect to the surface normal. The instantaneous angle of the visual inspection head (or of the light source in the visual inspection head) can be derived from the angle of the laser pointer with respect to the surface normal.

It is then ensured that the visual inspection system is correctly positioned with respect to the local surface and thus that a reliable measurement can be done. At block 400, the light source projects onto the local area and its reflection is determined. If the reflection deviates from an expected reflection, the surface may have a defect. False positives and false negatives may be avoided or reduced by always ensuring a correct projection (of a pattern) onto the part of the surface to be inspected.

In methods according to the present disclosure the indicated algorithm may be determined for subsequent areas of the surface to be inspected as the whole surface is inspected. In a practical implementation, an inspection trajectory may be determined for an object so that a sufficiently complete scan of a surface can be made. For each discrete point of the trajectory, the method of the example of FIG. 3 may be followed.

Although only a number of examples have been disclosed herein, other alternatives, modifications, uses and/or equivalents thereof are possible. Furthermore, all possible combinations of the described examples are also covered. Thus, the scope of the present disclosure should not be limited by particular examples, but should be determined only by a fair reading of the claims that follow.

What is claimed is:

1. A system for visually inspecting a surface of an object comprising
   a visual inspection head, and a module for controlling a position and/or an orientation of the visual inspection head with respect to the object,
   wherein the visual inspection head comprises a visual inspection module, and an angle controlling module for ensuring a predetermined angle of the visual inspection head with respect to an area to be inspected of the surface of the object,
   the visual inspection module comprising a light for projecting onto the surface and a sensor for determining a reflection of the light from the surface, and
   the angle controlling module comprising a pointer for projecting a light beam onto the area to be inspected, a camera for determining whether the light beam is reflected from the area to be inspected substantially perpendicularly,
   wherein the system is configured to move the visual inspection head relative to the object until the light beam is reflected substantially perpendicularly from the area to be inspected.

2. The system according to claim 1, further comprising a receiving surface for receiving the light beam after reflecting from the area to be inspected, and wherein the camera is arranged to determine a position of the reflected light beam.

3. The system according to claim 2, wherein the pointer is positioned on a first side of the receiving surface and the object is positioned on an opposite side of the receiving surface, the receiving surface comprising a hole for projection from the pointer onto the object.

4. The system according to claim 1, wherein the receiving surface is curved.

5. The system according to claim 1, wherein the angle measurement module further includes an optic element to deviate the reflected light beam towards the receiving surface or to the camera.

6. The system according to claim 1, wherein the module for controlling an orientation and/or position of the visual inspection head with respect to the object comprises actuators for moving the object.

7. The system according to claim 1, wherein the module for controlling a position and/or an orientation of the visual inspection head with respect to the object comprises actuators for moving the visual inspection head.

8. The system according to claim 1, further comprising a positioning module for changing an angle of the light source for projecting onto the surface and of the sensor for determining a reflection from the surface.

9. The system according to claim 1, wherein the pointer is a laser pointer.

10. A method for visually inspecting a surface of an object comprising
consecutively scanning different areas of the surface of the object by projecting a light onto the different areas and sensing a reflection from the different areas, the scanning comprising prior to projecting the light
for each of the different areas determining an angle of the light with respect to the surface normal of the area and comparing the angle of the light with a predetermined angle, and
adjusting the angle of the light with respect to the surface normal of the area if a difference between the angle of the light with respect to the surface normal and the predetermined angle is above a threshold, wherein
determining the angle of the light with respect to the surface normal of the area comprises projecting a laser beam on the area, receiving the laser beam reflection from the area, and determining whether the laser beam has been reflected substantially perpendicularly from the area.

11. The method according to claim 10, wherein comparing whether the laser beam has been reflected substantially perpendicularly from the area comprises comparing a position of the laser beam reflection with a predetermined area of a receiving surface.

12. The method according to claim 11, wherein the laser beam is positioned on a first side of the receiving surface and the object is positioned on an opposite side of the receiving surface, the receiving surface comprising a hole for projection from the pointer onto the object.

13. The method according to claim 10, further comprising determining a height of the laser beam with respect to the area.

14. The method according to claim 10, wherein adjusting the angle of the light with respect to the surface normal of the area comprising repositioning a visual inspection head with respect to the surface of the area, the visual inspection head including the laser beam, the receiving surface, and the light.

15. The method according to claim 10, wherein the reflected laser beam is deviated with an optic element towards a camera.

16. A system for visually inspecting a surface of an object comprising:
a visual inspection head, and
a module for controlling a predetermined angle of the visual inspection head with respect to a surface normal in an inspection point, wherein
the visual inspection head comprises a visual inspection module and an angle measurement module for determining an angle of the visual inspection head with respect to an area to be inspected of the surface of the object, wherein
the visual inspection module comprises a light source for projecting onto the surface and a sensor for determining a reflection from the surface, and wherein
the angle measurement module comprises a pointer for projecting a light beam onto the area to be inspected, a receiving surface for receiving the light beam after reflecting from the area to be inspected, and a camera for determining a position of the reflected light beam on the receiving surface.

17. The system according to claim 16, wherein the system is configured to move the visual inspection head relative to the object until the light beam is reflected substantially in the predefined angle relative to the surface normal.

18. The system according to claim 16, wherein the pointer is a laser pointer.

19. The system according to claim 16, wherein the receiving surface is curved.

20. The system according to claim 17, wherein the module for controlling the orientation of the visual inspection head with respect to the object comprises actuators for moving the visual inspection head.

* * * * *